United States Patent
Xiong et al.

(10) Patent No.: US 9,744,524 B2
(45) Date of Patent: Aug. 29, 2017

(54) MOLYBDENUM BASED COMPLEX OXIDE CATALYST, ITS PREPARATION METHOD AND USE

(71) Applicants: Shanghai HuaYi New Material Co., Ltd., Shanghai (CN); Shanghai HuaYi Acrylic Acid Co., Ltd., Shanghai (CN)

(72) Inventors: Desheng Xiong, Shanghai (CN); Yan Zhuang, Shanghai (CN); Xiaoxia Wang, Shanghai (CN); Ge Luo, Shanghai (CN); Tonghao Wu, Shanghai (CN); Jianxue Ma, Shanghai (CN); Xiadong Chu, Shanghai (CN); Jinhua Ji, Shanghai (CN)

(73) Assignees: Shanghai HuaYi New Material Co., Ltd., Shanghai (CN); Shanghai HuaYi Acrylic Acid Co., Ltd., Shanghai (CN)

( * ) Notice: Subject to any disclaimer, the term of this patent is extended or adjusted under 35 U.S.C. 154(b) by 0 days.

(21) Appl. No.: 14/960,946

(22) Filed: Dec. 7, 2015

(65) Prior Publication Data
US 2016/0184805 A1 Jun. 30, 2016

(30) Foreign Application Priority Data

Dec. 26, 2014 (CN) .......................... 2014 1 0848324

(51) Int. Cl.
| | |
|---|---|
| *B01J 23/887* | (2006.01) |
| *B01J 37/00* | (2006.01) |
| *B01J 37/04* | (2006.01) |
| *C07C 5/48* | (2006.01) |

(52) U.S. Cl.
CPC ....... *B01J 23/8876* (2013.01); *B01J 37/0036* (2013.01); *B01J 37/04* (2013.01); *C07C 5/48* (2013.01); *B01J 2523/00* (2013.01); *C07C 2523/02* (2013.01); *C07C 2523/04* (2013.01); *C07C 2523/18* (2013.01); *C07C 2523/28* (2013.01); *C07C 2523/745* (2013.01); *C07C 2523/75* (2013.01); *C07C 2523/755* (2013.01); *C07C 2523/887* (2013.01)

(58) Field of Classification Search
CPC .... B01J 23/8876; B01J 37/04; B01J 37/0036; B01J 2523/00; C07C 5/48; C07C 2523/75; C07C 2523/02; C07C 2523/755; C07C 2523/18; C07C 2523/04; C07C 2523/745; C07C 2523/887; C07C 2523/28

See application file for complete search history.

(56) References Cited

U.S. PATENT DOCUMENTS

| | | | | |
|---|---|---|---|---|
| 3,911,039 | A * | 10/1975 | Grasselli .............. | B01J 23/8876 502/306 |
| 4,423,281 | A * | 12/1983 | Yamamoto ............ | B01J 23/883 502/212 |
| 4,424,141 | A * | 1/1984 | Grasselli ............... | B01J 23/002 502/205 |
| 4,547,615 | A * | 10/1985 | Yamamoto ............... | C07C 5/48 502/305 |
| 2013/0023699 | A1* | 1/2013 | Macht .................. | B01J 23/8872 568/449 |
| 2013/0281748 | A1* | 10/2013 | Cha .......................... | B01J 8/04 585/302 |

OTHER PUBLICATIONS

M.Niwa, Y.Murakami; Study of Olefin Oxidation by Periodic-Pulse Technique II. Oxidative Dehydrogenation of 1-Butene Using Various Oxide Catalysts; Journal of Catalysts, 1972; vol. 27, pp. 27-33, Academic Press, Inc.

* cited by examiner

*Primary Examiner* — Anthony J Zimmer
(74) *Attorney, Agent, or Firm* — Quarles & Brady LLP

(57) ABSTRACT

Disclosed are a molybdenum based composite oxide catalyst, its preparation method and use. The catalyst has the following general formula: $BiMo_xM_yN_zO_a$; wherein M is one of V, Cr, Mn, Fe, Co, Ni and Cu, or a mixture of two or more of V, Cr, Mn, Fe, Co, Ni and Cu in any ratio; N is one of Na, K, Cs, Ca and Ba, or a mixture of two or more of Na, K, Cs, Ca and Ba in any ratio; $x=0.5\sim20$; $y=0.05\sim20$; $z=0.01\sim5$; a is a number satisfying the valance of each atom. The catalyst is prepared by the following method: firstly mixing a certain amount of the lead metal oxides according to the chemical proportion and then grinding the mixture with high-energy ball milling for a period of time to obtain the molybdenum based composite oxide catalyst. The catalyst exhibits excellent performance when using for preparation of butadiene by oxidative dehydrogenation of butene, and the preparation process is simple, controllable, and repeatable. Waste water or waste gas that is difficult to be treated is not produced during preparation.

10 Claims, No Drawings

MOLYBDENUM BASED COMPLEX OXIDE CATALYST, ITS PREPARATION METHOD AND USE

CROSS-REFERENCE TO RELATED APPLICATIONS

This application claims the benefit of Chinese Patent Application 201410848324.0, filed Dec. 26, 2014, which is incorporated herein by reference for all purposes.

STATEMENT REGARDING FEDERALLY SPONSORED RESEARCH OR DEVELOPMENT

Not applicable.

FIELD OF INVENTION

The present invention relates to a molybdenum based composite oxide catalyst, which exhibits high conversion rate of butene and high selectivity for butadiene. The present invention further relates to a method for preparing the catalyst and use of the catalyst in the preparation of butadiene by the oxidative dehydrogenation of butene.

BACKGROUND OF THE INVENTION

Butadiene is an important basic raw material used in the chemical industry and is a monomer used in a greatest amount among monomers used in the synthetic rubber industry. It is also an important intermediate used for the production of synthetic rubber and organic chemical raw material. Butadiene is widely used in synthesizing styrene butadiene rubber, cis-butadiene rubber, nitrile butadiene rubber, chloroprene rubber and ABS resin, etc.

Currently, butadiene is obtained mainly by extracting the by-product of naphtha cracking. However, with the development of light raw materials for ethylene and propylene, the yield of the cracking apparatus for naphtha is gradually reduced. Thus, the amounts of the extracted butadiene can not satisfy the ever-growing need of butadiene. There is an increased gap in the market for butadiene. Therefore, there is a need to develop a new process for the production of butadiene that is independent on alkene cracking. One feasible process is to prepare 1,3-butadiene by the oxidative dehydrogenation of butene, which is attractive by more and more people.

The catalysts currently used for catalyzing the oxidative dehydrogenation of butene mainly include ferrum based spinel catalyst, molybdenum based composite oxide catalyst and tin based catalyst. Two ferrum based catalysts, B-02 and H-198, had been developed in China in the 80's of the last century. Both have already been used in industry. The preferred advantages of the ferrite catalyst are little amount of oxygen-containing organic compounds in the by-product, and the waste water being readily treated. However, its disadvantages are low one-pass conversion rate, poor selectivity for butadiene, utilizing a large amount of water vapors as diluent gas, high energy consumption, and producing a large amount of waste waters.

The molybdenum based oxide catalyst exhibits high conversion rate and selectivity as compared with the ferrum based catalyst, and needs no water as a diluent gas in reaction. Thus, it has advantages in both the energy consumption and material consumption. The molybdenum based oxide catalyst generally comprises many metal components, its main active component is derived from bismuth molybdate, and other components are those derived from cobalt molybdate, ferrum molybdate and nickel molybdate as well as alkaline earth metal and alkali metal as co-catalysts [See, M. Niwa and Y. Murakami, J. Catal., 27, 26 (1972); A. P. V. Soares, L. D. Dimitrov, et al., Appl. Catal. A:Gen., 253, 191 (2003)].

Currently, there are two main methods for preparing the molybdenum based oxide catalyst, one is the co-precipitation method and the other is the direct drying method.

With respect to the direct drying method, U.S. Pat. No. 3,764,632 has disclosed a method for preparing a molybdenum based oxide catalyst by the direct drying method. Although the process of the method is simple, different metal elements in the catalyst are prone to isolate during drying because of the complicated catalyst components having different chemical properties. As a result, the components are not uniformly distributed in the catalyst, resulting in a complicated crystal phase structure, and, in turn, poor producing repeatability. In addition, the drying and firing steps of this method produce a large amount of waste gases containing nitrogen, chlorine, etc., troubling in the treatment of the waste gas.

With respect to the co-precipitation method, the current method for producing Bi/Mo/Fe composite oxide catalyst comprises to proceed with co-precipitation in a solution having an adjusted pH, obtaining a precursor. This method can enhance the activity of multi-component bismuth molybdate catalyst in a simple way. Although the co-precipitation method itself is simple, the metal ions may not be co-precipitated simultaneously or completely when preparing the catalyst by this method since different metal ions are precipitated at different pH values, resulting in the active ingredients not being uniformly distributed. In addition, the metal ions, such as cobalt ion, nickel ion and zinc ion, etc., may form a complex compound with the ammonium ion in the precipitating agent, which may be lost during filtration. Thus, it is difficult to precisely control the composition of the finally obtained catalyst, or a high cost is required to precisely control the composition of the finally obtained catalyst. As a result, the method is difficult to be practiced in an industrial scale. Furthermore, during preparation by the co-precipitation method, a lot of metal ion-containing waste water will be produced, which needs special treatment before discharge.

Mechanochemistry (or high-energy ball milling) is a method to prepare a superfine material. The mechanism of the mechanochemistry is to induce a chemical reaction or to induce change in composition, structure and property of the material by utilizing a mechanical energy, obtaining a new material. As a new technique, it can significantly reduce the activation energy of the reaction, decrease the size of crystal grain, greatly increase the activity of the powder, improve homogenous distribution of the particles, and enhance the interface binding among materials. It can also promote solid ion diffusion and induce a chemical reaction under low temperature to improve the properties, such as, degree of compaction, electric and thermal properties, of the material. Thus, it is a technique for preparing a material in an energy efficient and high efficient manner.

Considering the status of the prior art, there is still a need to develop a molybdenum based oxide catalyst used for preparing butadiene by the oxidative dehydrogenation of butene, which catalyst can not only exhibit high activity and selectivity, but also can be prepared in a relatively simple, controllable, and repeatable way with no active ingredients loss and reduced waste water and waste gas during preparation.

BRIEF SUMMARY OF THE INVENTION

Therefore, one object of the present invention is to provide a catalyst for preparing butadiene by the oxidative dehydrogenation of butene, which has high conversion rate of butene and high selectivity for butadiene.

Another object of the present invention is to provide a method for preparing the catalyst, which method is simple, readily to be repeated, no metallic ions loss, and no metallic ion containing-waste water and exhaust gas, as compared with the existing preparation methods.

Therefore, in one aspect, the present invention provides a molybdenum based composite oxide catalyst having the following formula:

$$BiMo_xM_yN_zO_a$$

wherein M is one of V, Cr, Mn, Fe, Co, Ni and Cu, or a mixture of two or more thereof in any ratio;

N is one of Na, K, Cs, Ca and Ba, or a mixture of two or more thereof in any ratio;

x=0.5~20;
y=0.05~20;
z=0.01~5;
a is a number satisfying the valance of each atom;
said catalyst is prepared by a method comprising the following steps:

(1) weighing bismuth molybdate and oxide precursors of other metal elements according to the proportions of ingredients in the above formula, grinding and sieving to obtain a mixture;

(2) transferring the mixture to a ball mill jar, ball milling same to produce the desired molybdenum based composite oxide catalyst.

In another aspect, the present invention provides a method for preparing the molybdenum based composite oxide catalyst of the present invention, comprising:

(1) providing bismuth molybdate and oxide precursors of other metal elements according to the proportions of ingredients in the above formula, grinding and sieving to obtain a mixture;

(2) transferring the mixture to a ball mill jar, ball milling same to produce the desired molybdenum based composite oxide catalyst.

In another aspect of the present invention, it is provided use of a ball milling method in the preparation of a catalyst for producing butadiene by the oxidative dehydrogenation of butene.

DETAILED DESCRIPTION OF THE INVENTION

Specific Mode for Carrying Out the Invention

1. Molybdenum Based Composite Oxide Catalyst

The present invention relates to a molybdenum based composite oxide catalyst, which exhibits excellent activity and selectivity for product in the reaction for producing butadiene by the oxidative dehydrogenation of butene.

The molybdenum based composite oxide catalyst of the present invention has the following structural formula:

$$BiMo_xMo_yN_zO_a$$

wherein M is one of V, Cr, Mn, Fe, Co, Ni and Cu, or a mixture of two or more thereof in any ratio; preferably is Fe, Co or Ni;

N is one of Na, K, Cs, Ca and Ba, or a mixture of two or more thereof in any ratio; preferably is K or Cs.

x in the above composite oxide catalyst is a range formed by any two, as end points, selected from the group consisting of 0.5, 20, 0.8, 18, 1.0, 15, 1.2 and 12. In one embodiment of the present invention, x is 0.5~20, preferably 0.8-18, more preferably 1.0-15, and most preferably 1.2-12.

y in the above composite oxide catalyst is a range formed by any two, as end points, selected from the group consisting of 0.05, 20, 0.08, 15, 0.10, 12, 0.12, 8, 0.15 and 5. In one embodiment of the present invention, y is 0.05~20, preferably 0.08-15, more preferably 0.10-12, even more preferably 0.12-8, and most preferably 0.15-5.

z in the above composite oxide catalyst is a range formed by any two, as end points, selected from the group consisting of 0.01, 5.0, 0.02, 4.0, 0.03, 2.0, 0.05, 1.0, 0.08 and 0.50. In one embodiment of the present invention, z is 0.01~5.0, preferably 0.02~4.0, more preferably 0.03~2.0, even more preferably 0.05~1.0, and most preferably 0.08~0.50.

a is a number satisfying the valance of each atom.

In one preferred embodiment of the present invention, the composite oxide catalyst of the present invention is selected from the group consisting of $Bi_{1.0}Mo_{1.0}Fe_{0.2}K_{0.05}O_c$, $Bi_{1.0}Mo_{1.5}Ni_{0.6}K_{0.1}O_c$, $Bi_{1.0}Mo_{1.5}Co_{0.2}Ca_{0.2}O_c$, or $Bi_{1.0}Mo_{1.5}Ni_{0.8}Ba_{0.2}O_c$, or a mixture of two or more thereof in any ratio.

2. Method for Preparing the Molybdenum Based Composite Oxide Catalyst

The molybdenum based composite oxide catalyst of the present invention can be prepared by the following steps.

(1) Weighing bismuth molybdate and oxide precursors of other metal elements according to the desired proportions of ingredients, grounding and sieving.

The oxide precursor may be a single oxide, or a mixture of metal oxides, depending on the steps of the method. Compounds that can be decomposed to form the oxide upon grinding can also be used. In one embodiment of the present invention, the metal oxide may be prepared by a precipitation method, a hydrothermal method, a thermal decomposition method or the like, or can be a commercially available one.

It is known that ball milling itself functions as mixing and grinding. Therefore, the steps of grinding and sieving before ball milling in the present invention are for shortening the duration of ball milling, because small particle size of the oxide can facilitate to shorten such duration. In one preferred embodiment of the present invention, after grinding and mixing, the metal oxides are sieved to 0.001-0.1 millimeters, preferably 0.01-0.09 millimeters, and more preferably 0.03-0.07 millimeters.

(2) Transferring the Sieved Mixture to a Ball Milling Jar and Ball Milling.

The material constituting the milling ball used in the present method is not specifically limited, as long as the milling ball will not un-advantageously affect the performance of the catalyst. In one embodiment of the present invention, a stainless steel ball is used as the milling ball. Generally, the mass ratio between the milling ball and the mixture to be ball milled (or between the milling ball and the mixture of the sieved oxides) in each pass is 50~5:1, preferably 40~10:1, and more preferably 30-20:1. If the mass ratio is too low, the duration for ball milling in each pass will be prolonged, resulting in reduced production efficiency of the catalyst. On the contrary, if the mass ratio is higher than the most preferred mass ratio, the yield of the catalyst and, in turn, the production efficiency, will be decreased.

In the present invention, the oscillation frequency of the ball mill is associated with the milling time. If the oscillation frequency of the ball mill is too low, a long milling time is required and the efficiency of preparing the catalyst will be very low. If the oscillation frequency of the ball mill is too high, the ball mill cannot be continuously operated due to un-timely heat emission. On the other hand, if the milling time is too short, the solid phase reaction among the metal oxides will be insufficient, resulting in low catalytic activity. On the contrary, if the milling time is extended beyond the most preferred milling time, the performance of the catalyst will not be further enhanced, sometimes the performance may even be decreased.

In one embodiment of the present invention, the oscillation frequency is 15-35 Hz, the milling time is 10-1,000 minutes; preferably, the oscillation frequency is 18-32 Hz, and the milling time is 100-900 minutes; more preferably the oscillation frequency is 20-30 Hz, and the milling time is 180-820 minutes; and most preferably, the oscillation frequency is 22-28 Hz and the milling time is 220-750 minutes.

Upon ball milling for a period of time, the active ingredients of the molybdenum based composite oxide catalyst can be directly obtained.

Atmosphere used during ball milling in the present invention is not specifically limited, which may be air, nitrogen gas or other inert gases.

In one embodiment of the present invention, the present method may further comprise steps of mixing the resultant active ingredients of the catalyst with graphite and molding to prepare the final catalyst. In one embodiment of the present invention, the addition amount of graphite comprises 2%~10%, preferably 5%~8%, and more preferably 6%~7%, of the total mass of the catalyst.

3. Use of the Molybdenum Based Composite Oxide Catalyst

The molybdenum based composite oxide catalyst of the present invention is useful in the preparation of butadiene by the oxidative dehydrogenation of butene, especially in a reaction condition that no water vapor is used as diluent gas. A suitable reaction may comprise the following steps: firstly, homogeneously mixing the butane (or a mixed hydrocarbons comprising butene), as starting material, and water vapor, air and a diluent gas; secondly, pre-heating same, and then passing the pre-heated mixed gases to a catalyst bed to perform dehydrogenation under the following reaction conditions: reaction temperature being 250-450° C., space velocity (with respect to butene as starting material) being 50~500 h$^{-1}$, molar concentration of butane being 1~20%, and molar ratio of butane, oxygen, water vapor, and diluent gas being 1:0.2~5:0~20:0~20; wherein the diluent gas is one of nitrogen gas, argon gas and helium gas.

In one embodiment of the present invention, the reaction for preparing butadiene by the oxidative dehydrogenation of butene comprises the following steps: preheating a mixture of butene as staring material and water vapor, air and a diluent gas, passing the mixture to a catalyst bed for the oxidative dehydrogenation under the following reaction conditions: reaction temperature being 300-420° C., space velocity (with respect to butene as the starting material) being 100~300 h$^{-1}$, molar concentration of butene being 4~12%, and molar ratio of butane, oxygen, water vapor, and diluent gas being 1:0.5~2.0:1~4:0~12, wherein the diluent gas is nitrogen gas.

In the present reaction for preparing butadiene by the oxidative dehydrogenation of butene, the molybdenum based composite oxide catalyst of the present invention is used in the catalyst bed.

The butene starting material may be one of 1-butene, trans-2-butene and cis-2-butene, or a mixture of any two or three of them.

In the present reaction for preparing butadiene by the oxidative dehydrogenation of butene, the conversion rate of butene and the selectivity for butadiene are calculated according to the following formulae, in which the amounts of butene and butadiene are weight amounts:

Conversion rate of butene (%)={[(the amount of butene before reaction)−(the amount of butene after reaction)]/(the amount of butene before reaction)}×100%

Selectivity of butadiene(%)=(the amount of butadiene produced)/(the amount of butene reacted)×100%

The molybdenum based composite oxide catalyst prepared by the method of the present invention exhibits high conversion rate of butene and high selectivity for butadiene. As demonstrated by the following examples, the conversion rate of butene by the molybdenum based composite oxide catalyst prepared by the present method is 80-98%, and the selectivity for butadiene is 90-97%, both of which are higher than those of the catalyst produced by the conventional co-precipitation method. In addition, when preparing the molybdenum based composite oxide catalyst, the present method has the advantages of simple, readily to be repeated, no metallic ion lose, and no metallic ion-containing waste water and exhaust gas.

The advantages of the present invention will be further demonstrated in view of the following examples.

EXAMPLE 1

1. Preparation of Catalyst 3.77 g β-Mo$_{2.0}$Bi$_{2.0}$O$_9$ and 1.6 g ferric oxide (containing 1.08 wt % potassium) were weighed and placed in a grinding bowl to manually grind for 5 minutes to homogenously mix same. The mixture was sieved to 0.001-0.1 millimeters and transferred to a 50 ml stainless steel ball milling jar. 100 g stainless steel balls were added and the mixture was milled for 4 hours under a ball mill rate of 25 Hz, obtaining a powder of molybdenum based composite oxide catalyst.

Upon analyzing by ICP, it was found that the composition of the catalyst was Mo$_{1.0}$Bi$_{1.0}$Fe$_{0.2}$K$_{0.05}$O$_x$. The molar ratio of Mo, Bi, Fe and K was identical to that in the starting material initially added, indicating no metal ion loss during preparation.

2. Evaluation of Performance of the Catalyst By the Dehydrogenation of Butane

The resultant catalyst powder was mixed with graphite by adding 3 wt % of graphite based on the total mass of the mixture. The mixed powder was molded to form particles having a size of 20-40 meshes and then loaded into a stainless steel tubular reactor to test the catalytic performance. Evaluation of the catalytic performance was conducted in the stainless steel tubular reactor having an inner diameter of 10 mm and a length of 350 mm. The volume of the catalyst was 12 ml.

The 1-butene, as starting material, was mixed with water vapor and air. The mixed gases was pre-heated to 300° C. and passed through the catalyst bed. The space velocity of 1-butene was 200 h$^{-1}$, the reaction temperature was 320° C., the molar ratio between air and butene was 5.7, the molar ratio between water vapor and butene was 2, the diluent gas was nitrogen gas and the concentration of butene was 8%.

20 hours after reaction (at that time the reaction was stable), the exhaust gas was subjected to online analysis by gas chromatograph (Agilent 7890).

According to the above equations, the conversion rate of 1-butene was 88% and the selectivity for butadiene was 94.8%.

COMPARATIVE EXAMPLE 1

1. Preparation of Catalyst by Calcination Rather Than Ball Milling

A molybdenum based composite oxide catalyst was prepared by a solid state reaction at high temperature. 3.77 g $\beta$-$Mo_{2.0}Bi_{2.0}O_9$ and 1.6 g ferric oxide (containing 1.08 wt % potassium) were weighed, placed in a grinding bowl, and manually grinded for 5 minutes to homogenously mix same. The mixture was sieved to 0.001-0.1 millimeters and transferred to a crucible. The crucible was placed in a muffle furnace for calcination. The atmosphere used for calcination was air, the calcination temperature was 550° C., and the calcination time was 4 hours.

Upon analysis by ICP, it was found that the composition of the catalyst was $Mo_{1.0}Bi_{1.0}Fe_{0.2}K_{0.05}O_x$. The molar ratio of Mo, Bi, Fe and K was identical to that in the starting material initially added.

2. Evaluation of Performance of the Catalyst by the Dehydrogenation of Butane

The performance of the catalyst was evaluated by the same experimental apparatus and method as those in Example 1. The space velocity of 1-butene was 200 $h^{-1}$, the reaction temperature was 320° C., the molar ratio between air and butene was 5.7, the molar ratio between water vapor and butene was 2, the diluent gas was nitrogen gas and the concentration of butene was 8%.

20 hours after reaction, the composition of the resultant gas was analyzed and calculated. The conversion rate of 1-butene was 38% and the selectivity for butadiene was 84.8%. As compared to the catalyst of Example 1, the catalyst prepared by solid state reaction at high temperature has poor activity and selectivity.

COMPARATIVE EXAMPLE 2

1. Preparation of Catalyst by Co-Precipitation

A molybdenum based composite oxide catalyst was prepared by a co-precipitation method. 80.8 g ferric nitrate and 485.10 g bismuth nitrate were dissolved in 1000 g distilled water acidified by nitric acid, forming solution A. 176.6 g ammonium metamolybdate was dissolved in 2,000 g distilled water and 5.05 g solid potassium nitrate was added thereinto, forming solution B. The molar ratio of Mo, Bi, Fe and K was 1:1:0.2:0.05. Solution A was added dropwise into solution B while stirring. PH of the mixture was adjusted by strong ammonia to 4.0, and the mixed solution was subjected to aging under ambient temperature for 2 hours. The solution was filtered and washed with distilled water until the filtrate has a neutral pH. The filter cake was dried at 110° C. to produce a loose solid. The resultant solid was ground and sieved. 2 wt % graphite was added into and mixed with the sieved solid. The mixture was pressed, broken up, and sieved to obtain particles having particle size of 10-20 meshes. The particles were calcined in a tubular furnace in a flowing air atmosphere under 520° C. for 3 hours, obtaining a molybdenum based composite oxide catalyst.

Upon analyzing the catalyst powder by ICP, it was found that the molar ratio of Mo, Bi, Fe and K in the catalyst was 0.8:1:0.2:0.02. Upon analyzing the filtrate by ICP, it was found relative larger amount of Mo ion, small amount of K ion and few or no Fe or Bi ions in the filtrate. The results showed that Mo, Bi, Fe and K were hardly precipitated completely when preparing the molybdenum based composite oxide by the co-precipitation method, and showed the element Mo ion loss seriously.

2. Evaluation of Performance of the Catalyst

The performance of the catalyst was evaluated by the same experimental apparatus and method as those in Example 1. The space velocity of 1-butene was 200 $h^{-1}$, the reaction temperature was 320° C., the molar ratio between air and butene was 5.7, the molar ratio between water vapor and butene was 2, the diluent gas was nitrogen gas and the concentration of butene was 8%. 20 hours after reaction, the composition of the resultant gas was analyzed and calculated. The conversion rate of 1-butene was 82% and the selectivity for butadiene was 84.8%. The activity of the catalyst prepared by the co-precipitation method almost similar to that of the catalyst in Example 1, but the former has poor selectivity, which was caused by loss of Mo and K.

COMPARATIVE EXAMPLE 3

1. Preparation of Catalyst by Co-Precipitation

A molybdenum based composite oxide catalyst was prepared by the co-precipitation method. 80.8 g ferric nitrate and 485.10 g bismuth nitrate were dissolved in 1000 g distilled water acidified with nitric acid, forming solution A. 220.75 g ammonium metamolybdate was dissolved in 2000 g distilled water, and 12.12 g solid potassium nitrate was added thereinto, forming solution B. The molar ratio of Mo, Bi, Fe and K was 1.25:1:0.2:0.12. Solution A was added dropwise into solution B while stirring. PH of the mixture was adjusted by strong ammonia to 4.0, and the mixed solution was subjected to aging under ambient temperature for 2 hours. The solution was filtered and washed with distilled water until the filtrate has a neutral pH. The filter cake was dried at 110° C. to produce a loose solid. The resultant solid was ground and sieved. 2 wt % graphite was added into and mixed with the sieved solids. The mixture was pressed, broken up, and sieved to obtain particles having particle size of 10-20 meshes. The particles were calcined in a tubular furnace in a flowing air atmosphere under 520° C. for 3 hours, obtaining a molybdenum based composite oxide catalyst.

Upon analyzing the catalyst powder by ICP, it was found that the molar ratio of Mo, Bi, Fe and K in the catalyst was 1:1:0.2:0.05. Upon analyzing the filtrate by ICP, it was found relative larger amount of Mo ion, small amount of K ion and few or no Fe or Bi ions. The results showed that Mo and K seriously lost. This Comparative Example produced such a solid catalyst that had the same element composition as that of the catalyst of Example 1 by increasing the addition amounts of ammonium metamolybdate and potassium nitrate as compared with Example 1 and Comparative Example 2.

2. Evaluation of Performance of the Catalyst

The performance of the catalyst was evaluated by the same experimental apparatus and method as those in Example 1. The space velocity of 1-butene was 200 $h^{-1}$, the reaction temperature was 320° C., the molar ratio between air and butene was 5.7, the molar ratio between water vapor and butene was 2, the diluent gas was nitrogen gas and the concentration of butene was 8%. 20 hours after reaction, the composition of the resultant gas was analyzed and calculated. The conversion rate of 1-butene was 85% and the selectivity for butadiene was 92.8%. Although the activity and selectivity of the catalyst in this Comparative Example were improved as compared with those in Comparative Example 2 by increasing the addition amount of ammonium metamolybdate and potassium nitrate, they were still inferior to the performance of the catalyst of Example 1.

EXAMPLE 2

1. Preparation of Catalyst 4.48 g α-$Mo_{2.0}Bi_{3.0}O_{12.0}$ and 0.45 g nickel oxide (containing 0.98 wt % potassium) were weighed and placed in a grinding bowl to manually grind for 5 minutes. The mixture was sieved to 0.001-0.1 millimeters and transferred to a 50 ml stainless steel ball milling jar. 70 g stainless steel balls were added and the mixture was milled for 2 hours under a ball mill rate of 28 Hz, obtaining a molybdenum based composite oxide catalyst.

Upon analyzing by ICP, it was found that the composition of the catalyst was $Mo_{1.0}Bi_{1.5}Ni_{0.6}K_{0.1}O_x$. The molar ratio of Mo, Bi, Fe and K was identical to that in the starting material initially added, indicating no metal ions loss during preparation.

2. Evaluation of Performance of the Catalyst by Dehydrogenation of Butane

The resultant catalyst powder was mixed with graphite by adding thereinto 3% by weight of graphite based on the total mass of the mixture. The mixed powder was molded to form particles having particle size of 20-40 meshes. The particle was loaded to a stainless steel tubular reactor to test the catalytic performance. Evaluation of the catalytic performance was conducted in the stainless steel tubular reactor having an inner diameter of 10 mm and a length of 350 mm. The volume of the catalyst was 12 ml.

The 1-butene starting material was mixed with water vapor and air. The mixed gas was pre-heated to 300° C. and passed through the catalyst bed. The space velocity of 1-butene was 200 $h^{-1}$, the reaction temperature was 380° C., the molar ratio between air and butene was 8, the molar ratio between water vapor and butene was 1, the diluent gas was nitrogen gas and the concentration of butene was 6%.

20 hours after reaction (at that time the reaction was stable), the exhaust gas was subjected to online analysis by gas chromatograph (Agilent 7890).

According to the above equations, the conversion rate of 1-butene was 80% and the selectivity for butadiene was 95.8%.

EXAMPLE 3

1. Preparation of Catalyst 4.48 g α-$Mo_{2.0}Bi_{3.0}O_{12.0}$, 0.16 g $Co_3O_4$ and 0.112 g CaO were weighed and placed in a grinding bowl to manually grind for 5 minutes, obtaining a homogenous mixture. The mixture was sieved to 0.001-0.1 millimeters and transferred to a 50 ml stainless steel ball milling jar. 100 g stainless steel balls were added and the mixture was milled for 4 hours under a ball mill rate of 25 Hz, obtaining a molybdenum based composite oxide catalyst.

Upon analyzing by ICP, it was found that the composition of the catalyst was $Mo_{1.0}Bi_{1.0}Co_{0.2}Ca_{0.2}O_x$. The molar ratio of Mo, Bi, Co and Ca was identical to that of the starting material initially added, indicating no metal ions loss.

2. Evaluation of Performance of the Catalyst by Dehydrogenation of Butane

The resultant catalyst powder was mixed with graphite by adding thereinto 3% by weight of graphite based on the total mass of the mixture. The mixed powder was molded to form particles having particle size of 20-40 meshes. The particle was loaded to a stainless steel tubular reactor to test the catalytic performance. Evaluation of the catalytic performance was conducted in the stainless steel tubular reactor having an inner diameter of 10 mm and a length of 350 mm. The volume of the catalyst was 12 ml.

The 1-butene starting material was mixed with water vapor and air. The mixed gas was pre-heated to 300° C. and passed through the catalyst bed. The space velocity of 1-butene was 300 $h^{-1}$, the reaction temperature was 380° C., the molar ratio between air and butene was 6, the molar ratio between water vapor and butene was 1, the diluent gas was nitrogen gas and the concentration of butene was 10%.

20 hours after reaction (at that time the reaction was stable), the exhaust gas was subjected to online analysis by gas chromatograph (Agilent 7890).

According to the above equations, the conversion rate of 1-butene was 82% and the selectivity for butadiene was 96.8%.

COMPARATIVE EXAMPLE 4

1. Preparation of Catalyst by Co-Precipitation 26.48 g ammonium heptamolybdate was weighed and dissolved in distilled water, forming solution A. 48.51 g bismuth nitrate, 5.86 g cobalt nitrate and 3.28 g calcium nitrate were weighed and dissolved in 200 ml distilled water acidified with nitric acid, forming solution B. Solution B was slowly added dropwise into solution A while stirring and, at the same time, ammonia was added dropwise to adjust the final pH of the solution to be 3.0. After addition, the resultant slurry was subjected to aging at 60° C. for 1 hour and then dried in an oven at 110° C. for 8 hours.

The resultant solid was broken up and sieved. 2 wt % of graphite was added. After mixing, the resultant mixture was pressed, broken up and sieved, obtaining particles having particle size of 10-20 meshes. The particles were calcined in a tubular furnace in a flowing air atmosphere under 510° C. for 10 hours, obtaining a composite oxide catalyst.

Upon analyzing by ICP, it was found that the composition of the catalyst was $Mo_{1.5}Bi_{1.0}Co_{0.2}Ca_{0.2}O_x$. No metal ion lost as compared with the element ratio initially added. However, during calcination, a great amount of pungent exhaust gases containing NOx were produced. Device for treating the exhaust gas must be equipped when industrially producing the catalyst by this method and the exhaust gas must be treated before discharge.

2. Evaluation of Performance of the Catalyst by Dehydrogenation of Butane

Evaluation of the catalytic performance was conducted in the stainless steel tubular reactor. The volume of the catalyst was 12 ml.

The starting material 1-butene was mixed with water vapor and air. The mixed gas was pre-heated to 300° C. and passed through the catalyst bed. The space velocity of 1-butene was 300 $h^{-1}$, the reaction temperature was 380° C., the molar ratio between air and butene was 6, the molar ratio between water vapor and butene was 1, the diluent gas was nitrogen gas and the concentration of butene was 10%. 20 hours after reaction (at that time the reaction was stable), the conversion rate of 1-butene produced by the catalyst was 84% and the selectivity for butadiene was 95.0%.

EXAMPLE 4

1. Preparation of Catalyst 4.48 g α-$Mo_{2.0}Bi_{3.0}O_{12.0}$, 0.6 g nickel oxide and 0.3068 g barium oxide were weighed and placed in a grinding bowl to manually grind for 5 minutes, obtaining a homogenous mixture. The mixture was sieved to 0.001-0.1 millimeters and transferred to a 50 ml stainless steel ball milling jar. 100 g stainless steel balls were added and the mixture was milled for 10 hours under a ball mill rate of 25 Hz, obtaining a molybdenum based composite oxide catalyst.

Upon analyzing by ICP, it was found that the composition of the catalyst was $Mo_{1.0}Bi_{1.0}Ni_{0.6}Ba_{0.2}O_x$. The molar ratio of Mo, Bi, Ni and Ba was identical to that in the starting material initially added, indicating no metal ions loss during preparation.

2. Evaluation of Performance of the Catalyst by Dehydrogenation of Butane

The resultant catalyst powder was mixed with graphite by adding 3% graphite based on the total mass of the mixture. The mixed powder was molded to form particles having particle size of 20-40 meshes. The particle was loaded to a stainless steel tubular reactor to test the catalytic performance. Evaluation of the catalytic performance was conducted in the stainless steel tubular reactor having an inner diameter of 10 mm and a length of 350 mm. The volume of the catalyst was 12 ml.

The 1-butene starting material was mixed with water vapor and air. The mixed gas was pre-heated to 300° C. and passed through the catalyst bed. The space velocity of 1-butene was 150 $h^{-1}$, the reaction temperature was 320° C., the molar ratio between air and butene was 5.7, the molar ratio between water vapor and butene was 2, the diluent gas was nitrogen gas and the concentration of butene was 8%.

20 hours after reaction (at that time the reaction was stable), the exhaust gas was subjected to online analysis by gas chromatograph (Agilent 7890).

According to the above equations, the conversion rate of 1-butene was 92% and the selectivity for butadiene was 93.8%.

By comparing the experimental results of the above examples with those of the comparative examples, it can be found that the process of the present method is simple, repeated readily, no metallic ions lost, and no metallic ion-containing waste water. Additionally, the catalyst prepared by the present method exhibits excellent performance when using for dehydrogenation of butene, i.e., exhibiting higher activity and selectivity for butadiene than those of the same catalyst prepared by a co-precipitation method.

What is claimed is:

1. A molybdenum based composite oxide catalyst having the following formula:

$BiMo_xM_yN_zO_a$ wherein M is one of V, Cr, Mn, Fe, Co, Ni or Cu;
N is one of Na, K, Cs, Ca and Ba, or a mixture of two or more thereof in any ratio;
x=0.5-20;
y=0.05-20;
z=0.01-5;
a is a number satisfying the valance of each atom;
wherein the catalyst is prepared by the method comprising the steps of:
(1) weighing bismuth molybdate and oxide precursors of other metal elements according to the proportions of ingredients in the above formula, grinding and sieving to obtain a mixture;
(2) transferring the mixture to a ball mill jar, ball milling same to produce the molybdenum based composite oxide catalyst.

2. The molybdenum based composite oxide catalyst according to claim 1, wherein M is one of V, Fe, Co or Ni; and N is K or Cs.

3. The molybdenum based composite oxide catalyst according to claim 1, wherein
X is 0.8-18; y is 0.08-15; and z is 0.02-4.0.

4. The catalyst according to claim 1, wherein the frequency of ball milling is 15-35 Hz, the time of ball milling is 10-1,000 minutes, the mass ratio between the milling ball and the mixture of oxides is 50-5:1.

5. The catalyst according to claim 4, wherein the mass ratio between the milling ball and the mixture of oxides is 30-10:1.

6. The catalyst according to claim 4, wherein the oscillation frequency of ball milling of the ball mill is 20-30 Hz, the time of milling is 180-820 minutes.

7. A method for forming a molybdenum based composite oxide catalyst having the following formula:

$BiMo_xM_yN_zO_a$ wherein M is one of V, Cr, Mn, Fe, Co, Ni and Cu;
N is one of Na, K, Cs, Ca and Ba, or a mixture of two or more thereof in any ratio;
x=0.5-20;
y=0.05-20;
z=0.01-5;
a is a number satisfying the valance of each atom;
said method comprising the steps of:
(1) weighing bismuth molybdate and oxide precursors of other metal elements according to the proportions of ingredients in the above formula, grinding and sieving to obtain a mixture;
(2) transferring the mixture to a ball mill jar, ball milling same to produce the desired molybdenum based composite oxide catalyst.

8. The method according to claim 7, wherein M is one of V, Fe, Co and Ni; and N is K or Cs.

9. The method according to claim 7, wherein X is 0.8-18; y is 0.08-15; and z is 0.02-4.0.

10. The method according to claim 7, wherein the frequency of ball milling is 15-35 Hz, the time of ball milling is 10-1,000 minutes, the mass ratio between the milling ball and the mixture of oxides is 50-5:1.

* * * * *